United States Patent [19]

Mori et al.

[11] Patent Number: 5,780,663

[45] Date of Patent: Jul. 14, 1998

[54] PROCESS FOR PRODUCING CARBONIC ACID DIESTER

[75] Inventors: Kenji Mori, Niigata; Takeshi Koyama, Yokohama, both of Japan

[73] Assignee: JGC Corporation, Tokyo, Japan

[21] Appl. No.: 835,804

[22] Filed: Apr. 16, 1997

[30] Foreign Application Priority Data

Apr. 17, 1996 [JP] Japan ................... 8-095568

[51] Int. Cl.⁶ .................................................. C07C 68/00
[52] U.S. Cl. ........................ 558/275; 55/220; 95/236; 252/189; 422/129; 558/260; 558/270; 558/274; 558/277
[58] Field of Search ........................ 558/275, 277

[56] References Cited

U.S. PATENT DOCUMENTS

| | | | |
|---|---|---|---|
| 3,653,810 | 4/1972 | Bratzler et al. | 95/236 |
| 5,274,163 | 12/1993 | Rechner et al. | 558/277 |
| 5,527,943 | 6/1996 | Rivetti et al. | 558/277 |
| 5,599,965 | 2/1997 | Kricsfalussy et al. | 558/277 |

OTHER PUBLICATIONS

Database CAPLUS on STN®, Chemical Abstracts Service, (Columbus, Ohio), Accession No. 1996:519632; Halat, A. et al., Pr. Nauk. Inst. Technol. Nieorg. Nawazow Miner. Politech. Wroclaw. 43, 17–29, (1995), abstract, 1996.

*Primary Examiner*—Michael G. Ambrose
*Attorney, Agent, or Firm*—Webb Ziesenheim Bruening Logsdon Orkin & Hanson, P.C.

[57] ABSTRACT

A process for producing a carbonic acid diester, a method of removing $CO_2$ and an absorbent for $CO_2$ and an apparatus therefor are provided and are capable of selective removing of $CO_2$ by absorption from a CO-containing gas admixed with $CO_2$ which is recovered from a reactor to thereby enable recycling CO to the reactor for use. The invention is characterized by (1) carrying out a reaction of an alcohol, carbon monoxide (CO) and oxygen in a reactor and withdrawing a gas (i) which contains CO and $CO_2$ produced as a by-product of the reaction from the reactor; (2) contacting the withdrawn gas (i) with an alcohol solution so that at least part of the $CO_2$ contained in the gas (i) is absorbed by the alcohol solution and removed from the gas (i), thereby obtaining a CO-containing gas (ii), and (3) recycling the CO-containing gas (ii) to the reactor. It is preferred that the gas (i) is subjected to vapor-liquid separation and a separated gas is contacted with the alcohol solution.

5 Claims, 2 Drawing Sheets

PROCESS FOR PRODUCING CARBONIC ACID DIESTER

FIELD OF THE INVENTION

The present invention relates to a process for producing a carbonic acid diester through an oxidative carbonylation of an alcohol. More particularly, the present invention is concerned with a process for producing a carbonic acid diester, in which, carbon dioxide is removed from a carbon monoxide containing gas admixed with carbon dioxide which is withdrawn from a reactor after reaction of an alcohol, carbon monoxide and oxygen for forming a carbonic acid diester and the resulting carbon monoxide containing gas is recycled to the reactor for effective use thereof, and apparatus therefor. Also, the present invention is concerned with a method of removing $CO_2$ from a gas containing carbon monoxide, and an absorbent for $CO_2$ for use in the production of the carbonic acid diester.

BACKGROUND OF THE INVENTION

The oxidative carbonylation of an alcohol is a common process for synthesizing a carbonic acid diester, in which an alcohol (represented by the formula ROH wherein R is an alkyl, a cycloalkyl or an aralkyl), carbon monoxide and oxygen react in the presence of a catalyst according to the scheme:

$$2ROH + CO + 1/2 O_2 \rightarrow (RO)_2CO + H_2O.$$

In this oxidative carbonylation of an alcohol, carbon dioxide ($CO_2$) is formed as a by-product by the combustion (complete oxidation) of the alcohol and CO. An excess amount of CO is fed into the reactor for enhancing the conversion of the alcohol. Thus, in the industrial process, it is desired that remaining CO is recycled.

When the above reaction is carried out in the liquid phase, the reaction product (carbonic acid diester), alcohol and water are substantially recovered in the liquid reaction mixture and the gas mainly composed of CO and $CO_2$ are withdrawn from the reactor.

On the other hand, when the above reaction is carried out in the gas phase, the gas withdrawn from the reactor contains CO, $CO_2$, reaction product (carbonic acid diester), alcohol, water, etc. This gas can be separated into a liquid phase containing carbonic acid diester, water and alcohol and a gas phase containing CO and $CO_2$ (vapor-liquid separation) by cooling the gas.

If the gas recovered directly from the reactor or recovered through the vapor-liquid separation from the reactor is continuously recycled to the reactor, $CO_2$ is accumulated in the reactor to deteriorate the reactivity. Therefore, the problem has been encountered that part of the reaction gas must be purged from the reactor.

Methods of treating the gas withdrawn from the above reactor and recycling the treated gas into the reactor have been proposed. For example, Japanese Patent Laid-open Publication No. 6(1994)-1754 proposed a process for producing a carbonic acid diester through reaction of an alcohol, CO and oxygen, in which, when $CO_2$ produced as a by-product should be removed from the recycle gas containing CO and oxygen from the reactor, part of the gas is passed through a $CO_2$ scrubber. Further, Japanese Patent Laid-open Publication No. 7(1995)-53475 proposed a process in which, in the circulation of (di)alkyl carbonate/alkanol mixture obtained by removing water from the gas stream from the reactor so that the concentration of water in the reactor is reduced, the gas of $CO/CO_2$ mixture from the top of the distillation column is contacted with NaOH in a scrubber to thereby remove $CO_2$ as $NaHCO_3$ before recycling the gas to the reactor.

However, the treatment of $CO_2$ with a basic solution such as NaOH has such drawbacks that not only is it difficult to recover alcohol and carbonic acid diester entrained by the gas but also the carbonic acid diester contained in the gas may be hydrolysed to alcohol and $CO_2$ and that the treatment of formed $NaHCO_3$ is necessary.

Japanese Patent Laid-open Publication No. 7(1995) 145109 proposed a method of removing HCl and copper salt arising from the catalyst contained in the reaction product in the production of DMC (dimethyl carbonate), in which the gas-vapor stream from the reactor is contacted with the fluid of synthesis process (water/methanol/DMC mixture liquid) at a temperature essentially equal to or less than the temperature of gas-vapor stream itself. In this method, the contact of the gas-vapor stream with the synthetic process fluid is performed at temperatures such as about 120° to 150° C. at which the gas-vapor stream from the reactor substantially does not condense. Under these conditions, $CO_2$ contained in the gas-vapor stream is not satisfactorily absorbed by the synthesis process fluid.

The absorption methods using amine solution and hot potassium carbonate solution are known as the popular processes for removing $CO_2$. However, the application of the basic absorbents as in these methods makes it difficult to recover carbonic acid diester and alcohol from the gas and carbonic acid diester tends to be hydrolyzed. Also, the method using dimethyl ether of polyglycol as an absorbent (SELECSOL process) is known as another method for removing $CO_2$. However, the method necessitates distillation and operation is not easy. Thus, it is not a suitable method for the production of a carbonic acid diester.

Therefore, in the production of a carbonic acid diester, it has been desired to develop a process in which $CO_2$ is effectively removed from the CO-containing gas withdrawn from the reactor to thereby enable recycling CO for use.

OBJECT OF THE INVENTION

The present invention has been made taking the above prior art into account. An object of the present invention is to provide a process for producing a carbonic acid diester through reaction of an alcohol, carbon monoxide and oxygen, in which $CO_2$ is removed by selective absorption from a CO-containing gas admixed with $CO_2$ withdrawn from the reactor and the resulting CO-containing gas is recycled to the reactor for effective use thereof. Other objects of the present invention are to provide a method of removing $CO_2$ from a carbon monoxide containing gas and an absorbent for $CO_2$ to be used in the production of the carbonic acid diester. A further object of the present invention is to provide an apparatus which can be suitably used in the above process.

SUMMARY OF THE INVENTION

In one aspect of the present invention, there is provided a process for producing a carbonic acid diester through an oxidative carbonylation of an alcohol, which comprises the steps of:

(1) carrying out a reaction of an alcohol, carbon monoxide (CO) and oxygen in a reactor and withdrawing a gas (i) which contains CO and carbon dioxide ($CO_2$) produced as a by-product of the reaction from the reactor;

(2) contacting the withdrawn gas (i) with an alcohol solution so that at least part of $CO_2$ contained in the gas (i) is removed by absorption, and (3) recycling a CO-containing gas (ii) having a reduced content of $CO_2$ obtained in step (2) to the reactor.

It is preferred that the gas (i) is subjected to vapor-liquid separation and a separated gas is contacted with the alcohol solution.

Further, the alcohol solution which contacted with the gas (i) can be heated and/or decompressed, so as to strip $CO_2$ therefrom, thereby enabling use as an alcohol solution for absorption of $CO_2$.

In the step (2), the alcohol solution may contain the carbonic acid diester.

The alcohol contained in the alcohol solution is preferably the same alcohol used as reaction raw material.

In another aspect of the present invention, there is provided a method of removing $CO_2$ from a gas in a process for producing a carbonic acid diester, which comprises contacting a $CO_2$-containing gas with an alcohol solution under conditions such that $CO_2$ can be absorbed by the alcohol solution.

In this method, the alcohol solution may contain the carbonic acid diester.

In a further aspect of the present invention, there is provided an absorbent for carbon dioxide to be used in producing a carbonic acid diester, which comprises an alcohol solution.

In this absorbent for carbon dioxide, the alcohol solution may contain carbonic acid diester.

In still a further aspect of the present invention, there is provided an apparatus for producing a carbonic acid diester, which comprises:

- a reactor (a) for synthesis of a carbonic acid diester in which an alcohol, carbon monoxide and oxygen react;
- a gas withdrawal path (b) through which a gas (i) is withdrawn from the reactor;
- a $CO_2$ absorber (c), connected to the gas withdrawal path, in which the gas (i) is contacted with an alcohol solution as an absorbent so that at least part of $CO_2$ contained in the gas (i) is removed by absorption; and
- a gas recycle path (d) through which the gas (ii) having a reduced content of $CO_2$ obtained after removal of $CO_2$ by absorption is recycled from the $CO_2$ absorber to the reactor.

The apparatus of the present invention may further comprise:

- a vapor-liquid separator for separating a liquid containing a carbonic acid diester from the gas (i), the vapor-liquid separator located in the middle of the gas withdrawal path (b) connecting the reactor and the $CO_2$ absorber.

The above apparatus of the present invention may still further comprise:

- an alcohol solution recovery path (e) through which the alcohol solution containing $CO_2$ which is absorbed in the $CO_2$ absorber is recovered;
- a $CO_2$ stripper (f) connected to the alcohol solution recovery path, in which $CO_2$ is stripped off from the alcohol solution containing $CO_2$; and
- an alcohol solution recycle path (g) through which the alcohol solution from which $CO_2$ is stripped off is recycled to the $CO_2$ absorber.

In addition to the above members (a) to (g), it is preferred that the apparatus of the present invention comprise:

- an alcohol solution feed path (h) branched from the alcohol solution recycle path (g), and by which part of the alcohol solution from which $CO_2$ is stripped off is fed into a carbonic acid diester purification system;
- a vapor-liquid separator (j) in which a liquid containing a carbonic acid diester is separated from the gas (i), the vapor-liquid separator being located in the middle of the gas withdrawal path connecting the reactor and the $CO_2$ absorber;
- a liquid reaction mixture feed path (k) through which a liquid reaction mixture which contains a carbonic acid diester separated in the vapor-liquid separator is fed into the carbonic acid diester purification system; and
- the carbonic acid diester purification system (m) in which water and the alcohol are separated from the alcohol solution and the liquid reaction mixture, thereby purifying the carbonic acid diester.

Also, it is preferred that the apparatus of the present invention comprise:

- the alcohol solution feed path (h);
- a liquid reaction mixture feed path (n) through which the liquid reaction mixture which contains a carbonic acid diester obtained in the reactor is fed into the carbonic acid diester purification system; and
- the carbonic acid diester purification system (m) in which water and the alcohol are separated from the alcohol solution and the liquid reaction mixture, thereby purifying the carbonic acid diester.

This apparatus is preferred to further comprise:

- a vapor-liquid separator (j) in which a liquid containing a carbonic acid diester is separated from the gas (i), the vapor-liquid separator being located in the middle of the gas withdrawal path connecting the reactor and the $CO_2$ absorber; and
- a liquid reaction mixture feed path (k) through which a liquid reaction mixture which contains a carbonic acid diester separated in the vapor-liquid separator is fed into the carbonic acid diester purification system.

DETAILED DESCRIPTION OF THE INVENTION

The process for producing a carbonic acid diester, method of removing $CO_2$, absorbent for carbon dioxide and apparatus therefor to be employed in the reaction of an alcohol, carbon monoxide and oxygen according to the present invention will be described in detail below with reference to the appended drawings.

(1) Reaction of alcohol, carbon monoxide and oxygen

Figure 1:
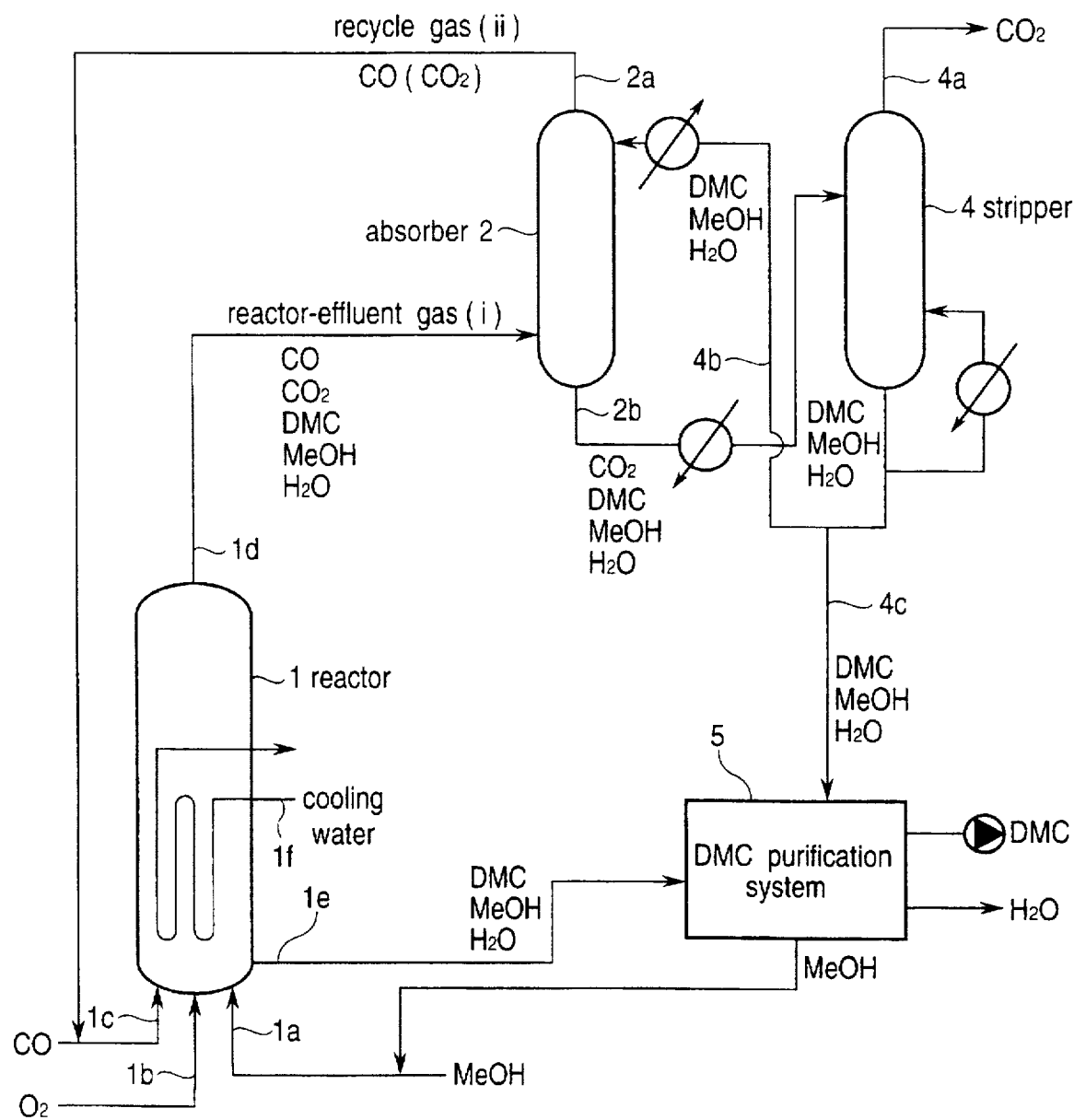
FIG. 1 is a process flow chart showing the process for producing a carbonic acid diester according to the present invention.

In the present invention, the synthesis of a carbonic acid diester through the oxidative carbonylation of an alcohol is performed by supplying an alcohol, carbon monoxide (CO) and oxygen to a reactor 1 as shown in FIG. 1 and reacting in the presence of a catalyst.

The reaction scheme is as follows:

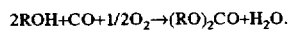

The reaction can be conducted not only in gas phase but also in liquid phase. An appropriate type of reactor can be selected. For example, when the reaction is conducted in the gas phase, a fixed bed or a fluidized bed can be used. On the other hand, when the reaction is conducted in the liquid phase, a gas-sparged stirred vessel or a bubble column can be used.

The reactor 1 may be provided with a cooler if in which, for example, water is used as a cooling medium.

In conducting this reaction, an inert gas such as nitrogen or hydrogen may be present in the reactor.

The alcohol (ROH) fed through a line 1a into the reactor 1 is, for example, an aliphatic alcohol, alicyclic alcohol and aromatic hydroxyl compound having 1 to 7 carbon atoms. Examples of suitable alcohols include monohydric alcohols such as methanol, ethanol, propanol, butanol, pentanol, hexanol, cyclopropanol, cyclobutanol, cyclopentanol, cyclohexanol and benzyl alcohol.

Of these, methanol and ethanol are preferred. The above alcohols can be used in combination.

The synthesis of dimethyl carbonate (DMC) from methanol (MeOH) as the ROH will be described below with reference to FIG. 1, which in no way limits the process for producing a carbonic acid diester according to the present invention.

Oxygen is fed through a line 1b and carbon monoxide is fed through a line 1c.

Suitable reaction conditions are selected depending on whether the reaction is conducted in the gas phase or in the liquid phase.

For example, when the reaction is conducted in the gas phase, it is preferred that the reaction temperature ranges from 70° to 350° C., especially, from 80° to 250° C. and that the reaction pressure ranges from atmospheric pressure to 35 kg/cm² G, especially, from 2 to 20 kg/cm² G.

Oxygen is preferably fed in an amount of 0.01 to 0.3 mol, still preferably, 0.05 to 0.2 mol per mol of the alcohol. Carbon monoxide is preferably fed in an amount of 0.2 to 100 mol per mol of the alcohol. It is still preferred for enhancing the conversion of the alcohol that carbon monoxide is fed in excess of stoichiometry. It is especially preferred that carbon monoxide is fed in an amount of 0.5 to 10 mol per mol of the alcohol, taking the electric power for circulating gas into account.

When the reaction is conducted in the liquid phase, it is preferred that the reaction temperature ranges from 80° to 200° C., especially, from 100° to 150° C. and that the reaction pressure ranges from 5 to 50 Kg/cm² G, especially, from 10 to 30 kg/cm² G. Oxygen and carbon monoxide are preferably fed in amounts as specified above.

The type of catalyst is not particularly limited as long as a carbonic acid diester can be synthesized by the reaction in the presence thereof. Examples of suitable catalysts include copper halides, palladium halides, copper halides with tertiary organophosphorus compound having phenyl or alkyl groups and copper oxyhalides comprising a copper halide and an alkali metal hydroxide or alkaline earth metal hydroxide. These can be used either as they are or in the form of being supported on a suitable carrier such as active carbon, titanium oxide, niobium oxide, silica, zirconium oxide, magnesium oxide or alumina.

(2) Absorption and Removal of $CO_2$

The reactor effluent gas (i) is withdrawn through a line 1d from the reactor 1 fed into an absorber 2 in which the gas (i) is contacted with an alcohol solution to thereby selectively absorb and remove $CO_2$ contained in the gas (i).

The gas (i) withdrawn from the reactor generally contains carbonic acid diester (DMC) as a desired product, water formed by the reaction, remaining alcohol (MeOH), remaining CO and $CO_2$ produced as a by-product.

Figure 2:
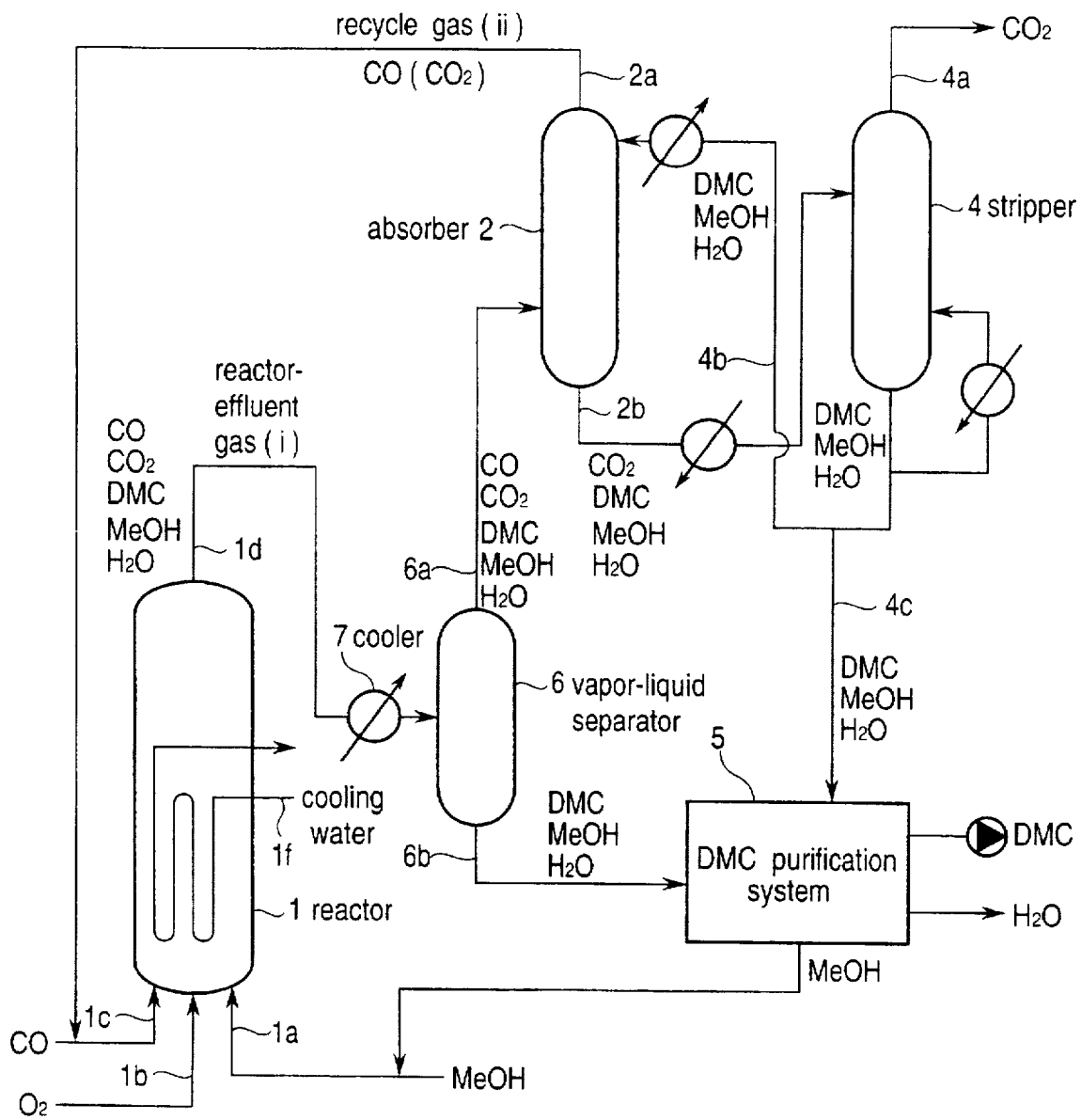
FIG. 2 is other process flow chart showing the process for producing a carbonic acid diester according to the present invention.

In the present invention, referring to FIG. 1, the gas (i) withdrawn from the reactor either may be directly fed into the absorber 2 in which the gas (i) is contacted with the alcohol solution or, referring to FIG. 2, may be subjected to vapor-liquid separation using vapor-liquid separator 6 to thereby separate a gas which is fed through a line 6a into the absorber 2 in which the gas is contacted with the alcohol solution.

More specifically, referring to FIG. 1, when, for example, most of the carbonic acid diester, water and alcohol is withdrawn through a line 1e in liquid phase, the gas (i) withdrawn through the line 1d can be directly fed into the absorber 2 in which the gas (i) is contacted with the alcohol solution. In this instance as well, the gas (i) can first be fed into a vapor-liquid separator 6 (not shown) in which vapor-liquid separation is conducted to thereby remove carbonic acid diester, water, alcohol, etc. from the gas (i) and then can be contacted with the alcohol solution.

Referring to FIG. 2, when the reaction product is withdrawn as a gas stream through the line 1d, it is preferred that the gas (i) is fed via a cooler 7 into a vapor-liquid separator 6 in which vapor-liquid separation is conducted and a separated gas is fed through a line 6a into the absorber 2.

The vapor-liquid separation reduces the load of the absorber 2.

In the vapor-liquid separator 6, it is preferred that the vapor-liquid separation of the gas (i) is conducted at a low temperature and a high pressure. From the economic viewpoint, however, it is preferred that the vapor-liquid separation is conducted at a temperature which is low but does not require a refrigerator and a pressure which is high but does not require a compressor. Specifically, the pressure may be in the same range as the above reaction pressure and, generally, the vapor-liquid separation is conducted under approximately the same pressure as in the reactor. The vapor-liquid separation temperature is preferred to be not higher than 40° C. A flash drum can be used as the vapor-liquid separator 6. For example, the gas (i) withdrawn through the line 1d can be cooled by a cooler 7 and subjected to vapor-liquid separation with the flash drum 6.

It is advantageous to use an outlet gas (ii) of the below described absorber for cooling of the reactor effluent gas (i). For example, a heat exchange may be executed between the reactor effluent gas (i) having been cooled by the cooler 7 and the outlet gas (ii) of the absorber to thereby lowering the temperature of the gas (i).

A gas composed mainly of CO and $CO_2$ can be obtained from the gas withdrawn from the reactor 1 by using a distillation column as the vapor-liquid separator 6.

The liquid separated by the vapor-liquid separator 6 contains a carbonic acid diester, an alcohol and water as main components thereof. It is preferred that this liquid is fed through a line 6b to the carbonic acid diester purification system 5, which will be described below, to thereby recover the carbonic acid diester and alcohol.

The separated gas withdrawn through a line 6a contains CO and $CO_2$ as main components and further contains small amounts of DMC, MeOH and water.

The alcohol solution used in the absorber 2 is preferred to be the same alcohol as used in the reaction. The alcohol solution may contain reaction products such as the carbonic acid diester and water in addition to the alcohol. For example, the liquid reaction mixture withdrawn through the line 1e (when the catalyst is contained, liquid obtained by separating the catalyst off) or the liquid reaction mixture withdrawn through the line 6b of the vapor-liquid separator can be used as the alcohol solution. Although the alcohol concentration of the alcohol solution is not particularly limited, it is generally preferred to range from 20 to 100% by weight.

The manner of the contact of the reactor gas effluent gas (i) with the alcohol solution is not particularly limited as long as it is conducted under such conditions that $CO_2$ can be absorbed in the alcohol solution. For example, the contact can be carried out under atmospheric or pressurized condition, preferably, at least 5 atm. From the view-point of easy operation, it is preferred that the contact is carried out under substantially the same pressure as in the reactor. The contact temperature is generally not higher than 30° C., preferably, not higher than 0° C. From the economic viewpoint, the contact temperature is preferred to be not lower than −30° C.

The contact of the reactor effluent gas (i) with the alcohol solution of low temperature causes the $CO_2$ contained in the gas (i) to be selectively absorbed by the alcohol solution. Thus, the recycle gas (ii) having at least part of the $CO_2$ removed by absorption can be obtained from an outlet 2a of the absorber.

In the absorber 2, it is satisfactory that the amount of absorbed $CO_2$ is the same as that formed in the reactor and there is no problem in that some concentration of $CO_2$ remains in the obtained recycle gas (ii).

Specifically, it is preferred that the ratio of the mount of $CO_2$ contained in the recycle gas (ii) to the mount of $CO_2$ absorbed by the alcohol solution from the gas (i) is in the range of about 0.1 to 20:1, especially, 2 to 10:1.

The increase of $CO_2$ concentration or partial pressure of reactor effluent gas to above extent facilitates the absorption of $CO_2$ by the alcohol solution.

The alcohol solution withdrawn through a line 2b from the absorber 2 contains not only alcohol and $CO_2$ but also the carbonic acid diester and water.

In the present invention, the alcohol solution is used as the absorbent for $CO_2$, so that the reaction product DMC contained in it is not hydrolyzed. Further, the carbonic acid diester and alcohol contained in the gas (i) can effectively be recovered in the alcohol solution.

(3) Recycle of CO

In the present invention, the gas (ii), having at least part of the $CO_2$ removed by absorption in the absorber 2, contains CO as a main component and is recycled through a line 2a to the reactor 1.

(4) Stripping of $CO_2$

In the present invention, it is preferred that the process is provided with the step of stripping off $CO_2$ dissolved in the alcohol solution withdrawn from the absorber 2.

Specifically, the alcohol solution withdrawn from the line 2b is fed into a stripper 4 in which the alcohol solution is heated and/or decompressed to thereby strip $CO_2$ through the line 4a while recycling the alcohol solution through a line 4b into the absorber 2.

A flash drum, for example, a stripping column can be used as the stripper 4.

FIGS. 1 and 2 show an example of stripper 4 provided with a heater (reboiler) at a bottom thereof. However, when a flash drum is used as the stripper, it is not needed to provide the stripper with a heater.

$CO_2$ is stripped off from the alcohol solution at a pressure which is lower than the operating pressure of the absorber, preferably, atmospheric pressure. When the stripper is a stripping column, it is preferred that the temperature of the column bottom is set at about the boiling point of the alcohol solution. When the stripper is a flash drum, the temperature can be set at any which is not lower than the melting point of the alcohol solution.

(5) Purification of carbonic acid diester

The alcohol solution recycled to the absorber 2 through the line 4b in item (4) contains MeOH, DMC and water as main components thereof. Part of this alcohol solution is preferably fed through a line 4c into a carbonic acid diester purification system 5 to separate and recover DMC (carbonic acid diester) and MeOH (alcohol) from the alcohol solution.

Further, referring to FIG. 2, the liquid reaction mixture which contains MeOH, DMC and water as main components is fed from the vapor-liquid separator 6 through the line 6b into the purification system 5, by which DMC and MeOH are separated and recovered from the liquid reaction mixture.

Still further, referring to FIG. 1, the liquid reaction mixture which contains MeOH, DMC and water as main components is fed from the bottom of the reactor 1 through the line 1e into the purification system 5, by which DMC and MeOH are separated and recovered from the liquid reaction mixture.

The MeOH thus separated in the purification system 5 is generally recycled to the reactor 1.

The carbonic acid diester can be purified by usual methods. For example, distillation is employed for separating the carbonic acid diester, alcohol and water from the alcohol solution and liquid reaction mixture.

The carbonic acid diester is accumulated in the alcohol solution. However, in the present invention, the carbonic acid diester entrained by the gas (i) from the reactor can effectively be recovered by feeding the alcohol solution from which $CO_2$ is stripped off to the carbonic acid diester purification system when using the same alcohol as that in the oxidative carbonylation.

Method of removing $CO_2$

As apparent from the foregoing, especially shown in the above "(2) Absorption and removal of $CO_2$", the present invention also provides a method of removing $CO_2$ from a gas, which comprises contacting a $CO_2$-containing gas with an alcohol solution under conditions such that $CO_2$ can be absorbed by the alcohol solution. The alcohol solution may contain the aforementioned carbonic acid diester, water and other substances.

$CO_2$ Absorbent

Furthermore, the present invention provides an absorbent for carbon dioxide for use in producing a carbonic acid diester, which comprises an alcohol solution.

The alcohol as a component of the absorbent for carbon dioxide of the present invention includes the alcohol solution used in the above "(2) Absorption and removal of $CO_2$", and is selected from among, for example, aliphatic alcohols, alicyclic alcohols and aromatic hydroxyl compounds having 1 to 7 carbon atoms. Of these, methanol and ethanol are preferably used.

It is preferred that the alcohol (ROH) has the same hydrocarbon group (R) as that of the carbonic acid diester $[(RO)_2CO]$.

The absorbent for carbon dioxide is preferred to be used in liquid phase from the viewpoint of efficiency of absorbing carbon dioxide. The absorbent for carbon dioxide may contain a carbonic acid diester, water and other substances in addition to the alcohol. Although the alcohol concentration of the absorbent is not particularly limited, it is generally preferred to range from 20 to 100% by weight.

The absorbent for carbon dioxide is contacted with a gas containing carbon dioxide under such conditions that carbon dioxide is absorbed by the absorbent. For example, the contact can be carried out under atmospheric or pressurized condition, preferably, at least 5 atm. From the viewpoint of operation, it is preferred that, in the production of a carbonic acid diester, the contact is carried out under substantially the same pressure as in the reactor. The contact temperature is generally not higher than 30° C., preferably, not higher than 0° C. From the economic viewpoint, the contact temperature is preferred to be not lower than −30° C.

The absorbent for carbon dioxide can be regenerated by a method which is not particularly limited. For example, the regeneration can be carried out by heating and/or decompressing so as to attain degassing.

The absorbent for $CO_2$ according to the invention comprises the alcohol solution, and is suitably used for preparing the carbonic acid diester.

Apparatus for producing carbonic acid diester

The apparatus for producing a carbonic acid diester according to the present invention is suitable for carrying out the process of the present invention. Referring to FIG. 1, this apparatus comprises:

- a reactor (a) designated "1" for synthesis of carbonic acid diester in which an alcohol, carbon monoxide and oxygen react;
- a gas withdrawal path (b) designated "$1d$" through which a gas (i) is withdrawn from the reactor;
- a $CO_2$ absorber (c), designated "2", connected to the gas withdrawal path $1d$, in which the reactor effluent gas is contacted with an alcohol solution as an absorbent so that at least part of $CO_2$ contained in the gas (i) is removed by absorption from the gas (i), thereby obtaining a gas (ii) having a reduced content of $CO_2$; and
- a gas recycle path (d) designated "$2a$" through which the gas (ii) is recycled from the $CO_2$ absorber 2 to the reactor.

Referring to FIG. 2, the apparatus of the present invention may further comprise:

- a vapor-liquid separator (j) designated "6" in which a liquid containing a carbonic acid diester is separated from the gas (i), the vapor-liquid separator being located in the middle of the gas withdrawal path (b) connecting the reactor (a) and the $CO_2$ absorber (c).

In addition to the above members (a) to (d), the apparatus of the present invention may comprise:

- an alcohol solution recovery path (e) designated "$2b$" through which the alcohol solution including absorbed $CO_2$ which is absorbed in the $CO_2$ absorber 2 is recovered;
- a $CO_2$ stripper (f), designated "4", connected to the alcohol solution recovery path $2b$ in which $CO_2$ is stripped off from the alcohol solution containing $CO_2$; and
- an alcohol solution recycle path (g) designated "$4b$" through which the alcohol solution from which $CO_2$ is stripped off is recycled to the $CO_2$ absorber.

In addition to the above members (a) to (g), it is preferred that, referring to FIG. 2, the apparatus of the present invention comprise:

- an alcohol solution feed path (h), designated "$4c$", branched from the alcohol solution recycle path $4b$, and by which part of the alcohol solution from which $CO_2$ is stripped off is fed into a carbonic acid diester purification system 5;
- a vapor-liquid separator (j) designated "6" in which a liquid containing a carbonic acid diester is separated from the reactor effluent gas (i), the vapor-liquid separator being located in the middle of the gas withdrawal path $1d$ connecting the reactor 1 and the $CO_2$ absorber 2;
- a liquid reaction mixture feed path (k) designated "$6b$" through which a liquid reaction mixture which contains a carbonic acid diester separated in the vapor-liquid separator is fed into the carbonic acid diester purification system; and
- the carbonic acid diester purification system (m) designated "5" in which water and the alcohol are separated from the alcohol solution and the liquid reaction mixture, thereby purifying the carbonic acid diester.

Also, in addition to the above members (a) to (g), it is preferred that the apparatus of the present invention comprise:

- an alcohol solution feed path (h), designated "$4c$", branched from the alcohol solution recycle path $4b$ and by which part of the alcohol solution from which $CO_2$ is stripped off is fed into a carbonic acid diester purification system 5;
- a liquid reaction mixture feed path (n) designated "$1e$" through which a liquid reaction mixture which contains a carbonic acid diester obtained in the reactor 1 is fed into the carbonic acid diester purification system; and
- the carbonic acid diester purification system (m) designated "5" in which water and the alcohol are separated from the alcohol solution and the liquid reaction mixture, thereby purifying the carbonic acid diester.

Referring to FIG. 2, this apparatus is preferred to further comprise:

- a vapor-liquid separator (j) designated "6" in which a liquid containing a carbonic acid diester is separated from the reactor effluent gas (i), the vapor-liquid separator being located in the middle of the gas withdrawal path connecting the reactor 1 and the $CO_2$ absorber 2; and
- a liquid reaction mixture feed path (k) designated "$6b$" through which a liquid reaction mixture which contains a carbonic acid diester separated in the vapor-liquid separator is fed into the carbonic acid diester purification system.

EFFECT OF THE INVENTION

In accordance with the process for producing the carbonic acid diester through reaction of an alcohol, carbon monoxide and oxygen, the carbon monoxide-containing gas withdrawn from the reactor can be recycled to the reactor for effective use thereof. Further, the apparatus for producing the carbonic acid diester in accordance with the present invention can effectively conduct the process for producing the carbonic acid diester.

EXAMPLE

The present invention will now be illustrated in greater detail with reference to the following Examples, which in no way limit the scope of the invention.

The catalyst used in Examples 1 and 2 and Comparative Example 1 was prepared in the following manner.

[Preparation of catalyst]

37 Kg of cupric chloride dihydrate was dissolved in 100 l of distilled water, to give a cupric chloride solution. On the other hand, 13 Kg of sodium hydroxide was dissolved in 100 l of distilled water, to yield an aqueous sodium hydroxide solution.

100 Kg of active carbon was impregnated with 50 l of the cupric chloride solution and dried at 100° C. for 3 hr flowing inert gas (nitrogen gas). The resulting active carbon supporting cupric chloride was cooled, impregnated with 40 l of the aqueous sodium hydroxide solution and dried at 100° C. for 3 hr flowing inert gas, thereby obtaining a catalyst A (containing 6% by weight of Cu, molar ratio of OH/Cu=1.2). The Cu content was calculated by the formula:

$$\text{Cu content} = \frac{\text{wt. of Cu}}{\text{wt. of Cu halide} + \text{wt. of active carbon}} \times 100. \quad (1)$$

Example 1

DMC (dimethyl carbonate) was produced according to the process shown in FIG. 2. Namely, CO was fed through the line 1c at a rate of 6.6 kg/h, $O_2$ was fed through the line 1b at a rate of 0.6 kg/h and vaporized methanol was fed through the line 1a at a rate of 3.9 kg/h into the fluidized bed reactor 1 of 100 mm of inside diameter and 1500 mm of static catalyst height and react in the presence of the catalyst described above.

The reaction pressure was 9 atm. and the reaction temperature was controlled at 150° C. by circulating cooling water through the coil if (4 mm in inside diameter) equipped in the reactor.

The gas (i) withdrawn through the reactor outlet line 1d was cooled to 30° C. by the cooler 7 and fed into the flash drum 6 under the reaction pressure in which the vapor-liquid separation was carried out. The gas separated by the flash drum 6 was led through the line 6a into the absorber 2. On the other hand, the separated liquid was fed through the line 6b to the purification system 5.

Packed columns having an inside diameter of 80 mm and a packed bed height of 1500 mm were used as the absorber 2 and the stripper 4. In the absorber 2, $CO_2$ was absorbed by cold methanol at about 9 atm and -20° C. In the stripper 4, $CO_2$ was stripped off by reducing the pressure to atmospheric pressure and raising the temperature of the bottom of the column to 70° C.

Subsequently, the gas (ii) from the outlet 2a of the absorber 2 was compressed and recycled to the reactor 1 and the supplies of fresh CO and $O_2$ were reduced to 0.8 and 0.5 kg/h, respectively. While maintaining these conditions, the reaction was continued for 20 hr. After the concentration of DMC in the absorbent (alcohol solution) became 10% by weight, the absorbent was intermittently withdrawn through the line 4c in an average amount of to 220 g per hour and fed to the purification system 5, and the same amount of fresh methanol was added to the absorbent.

Table 1 lists the flow rate and composition (% by weight) of each of the gas at reactor outlet 1d, gas at flash drum outlet 6a, liquid at flash drum outlet 6b, gas at absorber outlet 2a and gas at stripper outlet 4a, when the composition at each part became substantially constant.

TABLE 1

|  | reactor outlet gas | flash drum outlet gas | flash drum outlet liquid | absorber outlet gas | stripper outlet gas |
|---|---|---|---|---|---|
| flow rate (kg/h) | 12.8 | 8.3 | 4.5 | 7.7 | 0.3 |
| composition (wt. %) |  |  |  |  |  |
| CO | 48 | 74 | 0.2 | 79 | 10 |
| $O_2$ | 1 | 2 | trace | 2 | 0.4 |
| $CO_2$ | 14 | 21 | 1 | 19 | 80 |
| MeOH | 21 | 2 | 55 | 0.1 | 3 |
| DMC*[1] | 13 | 1 | 35 | 0.1 | 2 |
| $H_2O$ | 3 | 0.1 | 8 | trace | trace |
| LE*[2] | 0.3 | 0.2 | 1 | trace | 3 |

DMC*[1] ... dimethyl carbonate
LE*[2] ... low boiling impurity

Comparative Example 1

Oxidative carbonylation of methanol was conducted at 150° C. under 9 atm in the same reactor as in Example 1. The reaction was initiated by feeding CO, $O_2$ and methanol at respective flow rates of 6.6, 0.6 and 3.9 kg/h in the same manner as in Example 1. The reactor effluent gas was cooled to 30° C. and fed into the flash drum under the reaction pressure. The separated liquid was fed to the purification system and the separated gas was compressed and directly recycled to the reactor. The supplies of fresh CO and $O_2$ to the reactor were reduced to 0.8 and 0.5 kg/h, respectively.

The recycle gas was continually analyzed. The increase of the $CO_2$ concentration of the gas was detected, so that, from 10 hr later, 1.2 kg/h of the gas separated at the flash drum was purged outside the system. 250 g/h of $CO_2$ was contained in this gas, which was substantially identical with the amount of $CO_2$ formed by the reaction.

The purged gas contained 21 g/h of methanol and 15 g/h of DMC.

As apparent from the results of Example 1 and Comparative Example 1, the present invention enables not only effectively removing $CO_2$ from the reactor effluent gas but also remarkably reducing the losses of CO, methanol and DMC, so that the recycling of CO is satisfactorily attained to thereby enable efficient production of the carbonic acid diester.

Example 2

CO, $O_2$ and vaporized ethanol were fed at respective flow rates of 5.6, 0.5 and 4.6 kg/h into the same fluidized bed reactor 1 as in Example 1.

The reaction pressure was 9 atm. and the reaction temperature was controlled at 150° C. by circulating cooling water through the coil lf (4 mm in inside diameter) placed in the reactor.

The gas (i) withdrawn through the reactor outlet line 1d was cooled to 30° C. by the cooler 7 and fed into the flash drum 6 under the reaction pressure by which the vapor-liquid separation was carried out. The gas separated in the flash drum 6 was led through the line 6a into the absorber 2. On the other hand, the separated liquid was fed through the line 6b to the purification system 5.

Packed columns having an inside diameter of 80 mm and a packed bed height of 1500 mm were used as the absorber 2 and the stripper 4. In the absorber 2, $CO_2$ was absorbed by cold ethanol at about 9 atm and -15° C. In the stripper 4, $CO_2$ was stripped by reducing the pressure to atmospheric pressure and raising the temperature of the bottom of the column to 82° C.

Subsequently, the gas (ii) from the outlet 2a of the absorber 2 was compressed and recycled to the reactor 1 and the supplies of fresh CO and $O_2$ were reduced to 0.6 and 0.4 kg/h, respectively. While maintaining these conditions, the reaction was continued for 20 hr. After the concentration of diethyl carbonate (DEC) in the absorbent became 10% by weight, the absorbent was intermittently withdrawn through the line 4c in an average amount of 90 g per hour and fed to the purification system 5, and the same amount of fresh ethanol was added to be absorbent.

Table 2 lists the flow rate and composition (% by weight) of each of the gas at reactor outlet 1$_d$, gas at flash drum outlet 6a, liquid at flash drum outlet 6b, gas at absorber outlet 2a and gas at stripper outlet 4a, when the composition at each part became substantially constant.

TABLE 2

|  | reactor outlet gas | flash drum outlet gas | flash drum outlet liquid | absorber outlet gas | stripper outlet gas |
| --- | --- | --- | --- | --- | --- |
| flow rate (kg/h) | 11.8 | 6.7 | 5.1 | 6.4 | 0.2 |
| composition (wt. %) | | | | | |
| CO | 44 | 77 | 0.3 | 81 | 12 |
| $O_2$ | 1 | 2 | trace | 1 | 0.2 |
| $CO_2$ | 12 | 20 | 0.9 | 17 | 87 |
| EtOH | 29 | 1 | 66 | 0.1 | trace |
| DEC*[1] | 11 | 0.3 | 26 | trace | trace |
| $H_2O$ | 2 | 0.1 | 5 | trace | trace |
| LE*[2] | 0.4 | 0.1 | 1 | trace | 1 |

DEC*[1] ... diethyl carbonate
LE*[2] ... low boiling impurity

What is claimed is:

1. A process for producing a carbonic acid diester through an oxidative carbonylation of an alcohol, which comprises the steps of:
   (1) carrying out a reaction of an alcohol, carbon monoxide (CO) and oxygen in a reactor and withdrawing a gas (i) which contains CO and carbon dioxide ($CO_2$) produced as a by-product of the reaction from the reactor;
   (2) contacting the withdrawn gas (i) with an alcohol solution so that at least part of $CO_2$ contained in the gas (i) is removed by absorption, and
   (3) recycling a CO-containing gas (ii) having a reduced content of $CO_2$ obtained in step (2) to the reactor.

2. The process as claimed in claim 1, wherein, in the step (2), the gas (i) is subjected to vapor-liquid separation and a separated gas is contacted with the alcohol solution.

3. The process as claimed in claim 1, wherein the alcohol solution contacted with the gas (i) is heated and/or decompressed in order to strip $CO_2$ therefrom and is used as an alcohol solution for absorption of $CO_2$.

4. The process as claimed in claim 1, wherein, in the step (2), the alcohol solution contains the carbonic acid diester.

5. The process as claimed in claim 1, wherein the alcohol contained in the alcohol solution is the same alcohol used to prepare the carbonic acid diester.

* * * * *

UNITED STATES PATENT AND TRADEMARK OFFICE
CERTIFICATE OF CORRECTION

PATENT NO. : 5,780,663
DATED : July 14, 1998
INVENTOR(S) : Kenji Mori and Takeshi Koyama It is certified that error appears in the above-identified patent and that said Letters Patent is hereby corrected as shown below:

Column 5 Line 4 "cooler if" should read --cooler 1f--.

Column 5 Line 8 "line 1a" should read --line 1a--.

Column 7 Line 28 "mount" should read --amount--.

Column 7 Line 29 "mount" should read --amount--.

Column 11 Line 26 "line 1c" should read --line 1c--.

Column 11 Line 28 "line 1a" should read --line 1a--.

Column 11 Line 35 "coil if" should read --coil 1f--.

Column 12 Line 55 "coil 1f" should read --coil 1f--.

Signed and Sealed this

Eighth Day of June, 1999

Attest:

Q. TODD DICKINSON

*Attesting Officer*   Acting Commissioner of Patents and Trademarks